United States Patent [19]
Himmelsbach et al.

[11] Patent Number: 5,958,952
[45] Date of Patent: Sep. 28, 1999

[54] SUBSTITUTED PHENYLAMINDINES, MEDICAMENTS CONTAINING THESE COMPOUNDS AND PROCESS FOR PRODUCING THEM

[75] Inventors: Frank Himmelsbach, Mittelbiberach; Volkhard Austel, Biberach; Günther Linz, Mittelbiberach; Helmut Pieper, Biberach; Brian Guth, Warthausen; Johannes Weisenberger, Biberach, all of Germany

[73] Assignee: Dr. Karl Thomae GmbH, Biberach, Germany

[21] Appl. No.: 08/945,611

[22] PCT Filed: Apr. 18, 1996

[86] PCT No.: PCT/EP96/01615

§ 371 Date: Dec. 17, 1997

§ 102(e) Date: Dec. 17, 1997

[87] PCT Pub. No.: WO96/33970

PCT Pub. Date: Oct. 31, 1996

[30] Foreign Application Priority Data

Apr. 27, 1995 [DE] Germany ............ 195 15 500

[51] Int. Cl.⁶ .......... A61K 31/155; A61K 31/445; C07D 211/06; C07D 211/74
[52] U.S. Cl. .......... 514/327; 514/252; 514/256; 514/318; 514/326; 514/328; 514/331; 544/238; 544/335; 544/336; 546/194; 546/209; 546/210; 546/220; 546/221; 546/231
[58] Field of Search ............ 546/220, 221, 546/231; 514/327, 328, 331

[56] References Cited

U.S. PATENT DOCUMENTS

| | | | |
|---|---|---|---|
| 5,378,727 | 1/1995 | Bovy et al. | 514/465 |
| 5,399,585 | 3/1995 | Alig et al. | 514/438 |
| 5,455,348 | 10/1995 | Austel et al. | 544/238 |
| 5,591,769 | 1/1997 | Himmelsbach et al. | 514/423 |

FOREIGN PATENT DOCUMENTS

| | | |
|---|---|---|
| 0381033 | 8/1990 | European Pat. Off. . |
| 0483667 | 5/1992 | European Pat. Off. . |
| 0528369 | 2/1993 | European Pat. Off. . |
| 0539343 | 4/1993 | European Pat. Off. . |

OTHER PUBLICATIONS

Takada et al., Chemical Abstracts, vol. 126, abstract 317393, 1997.
Ohshika et al., Chemical Abstracts, vol. 126, abstract 157821, 1997.
Fukushi et al., Chemical Abstracts, vol. 126, abstract 31374, 1997.
Ono et al., Chemical Abstracts, vol. 125, abstract 114709, 1996.

*Primary Examiner*—Richard L. Raymond
*Attorney, Agent, or Firm*—R. P. Raymond; M-E. M. Devlin; A. R. Stempel

[57] ABSTRACT

The present invention relates to phenyl amidines of general formula (I),

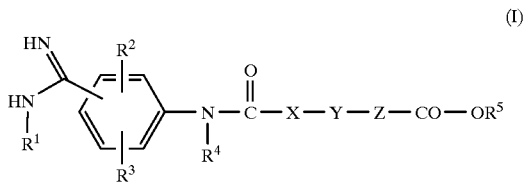

(I)

in which $R^1$ to $R^5$ are as defined in claim 1, their tautomers, their stereoisomers and their mixtures and their salts, especially their physiologically acceptable salts with inorganic or organic acids or bases also having valuable pharmacological properties, preferably aggregation-limiting effects, producing them.

11 Claims, No Drawings

SUBSTITUTED PHENYLAMIDINES, MEDICAMENTS CONTAINING THESE COMPOUNDS AND PROCESS FOR PRODUCING THEM

This application is a 371 of PCT/EP96/01615, filed Apr. 18, 1996.

The invention relates to phenylamidines of general formula

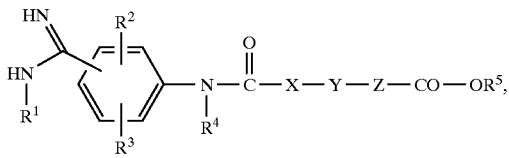

(I)

the tautomers thereof, the stereoisomers including the mixtures thereof and the salts thereof, particularly the physiologically acceptable salts thereof with inorganic or organic acids or bases, which have valuable pharmacological properties, preferably aggregation-inhibiting properties, pharmaceutical compositions containing these compounds, the use thereof and processes for preparing them.

In the above general formula I

X and Z, which may be identical or different, each denote a straight-chained alkylene group, which may optionally be substituted by one or two alkyl groups, by an alkenyl group having 2 to 4 carbon atoms, by an alkynyl group having 2 to 4 carbon atoms, by an aryl, arylmethyl, heteroaryl or heteroarylmethyl group, Y denotes a 5- to 7-membered cycloalkylene group optionally substituted by one or two alkyl groups, a pyrrolidinylene, piperidinylene or azacycloheptylene group optionally substituted by one or two alkyl groups, whilst in the abovementioned rings one or two methylene groups adjacent to a nitrogen atom may be replaced by a carbonyl group, a piperazinylene or 1,4-diazacycloheptylene group optionally substituted by one or two alkyl groups, whilst in the abovementioned rings one or two methylene groups adjacent to a nitrogen atom may be replaced by a carbonyl group, $R^1$ denotes a hydrogen atom, an alkyl, 1,1,1-trifluoroethyl or alkyloxycarbonyl group, an arylalkyloxycarbonyl group having 1 to 3 carbon atoms in the alkyl moiety or a group of formula

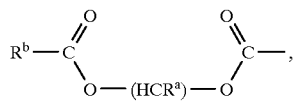

wherein $R^a$ denotes a hydrogen atom or an alkyl group and
$R^b$ denotes an alkyl group or a 3- to 7-membered cycloalkyl group, $R^2$ and $R^3$, which may be identical or different, each denote a hydrogen, fluorine, chlorine, bromine or iodine atom, an alkyl, trifluoromethyl or alkoxy group, $R^4$ denotes a hydrogen atom, an alkyl, arylalkyl or heteroarylalkyl group and $R^5$ denotes a hydrogen atom, an alkyl group having 1 to 8 carbon atoms, a 4- to 7-membered cycloalkyl group optionally substituted by one or two alkyl groups, an aryl or arylalkyl group or a group of formula

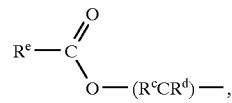

wherein $R^c$ denotes a hydrogen atom or an alkyl group, $R^d$ denotes a hydrogen atom or an alkyl group and $R^e$ denotes an alkyl or alkoxy group, a 3- to 7-membered cycloalkyl group or a 5- to 7-membered cycloalkoxy group, wherein, unless otherwise stated, the aryl moieties specified in the definitions of the above groups refer to a phenyl group, which may be monosubstituted by $R^6$, mono-, di- or trisubstituted by $R^7$ or monosubstituted by $R^6$ and additionally mono- or disubstituted by $R^7$, wherein the substituents may be identical or different and $R^6$ denotes a cyano, carboxy, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoralkyl, trifluoromethoxy, nitro, amino, alkylamino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl- or dialkylaminosulphonyl group and $R^7$ denotes an alkyl, hydroxy or alkoxy group, a fluorine, chlorine, bromine or iodine atom, wherein two groups $R^6$, if they are attached to adjacent carbon atoms, may also denote an alkylene group having 3 to 6 carbon atoms, a 1,3-butadiene-1,4-diylene group or a methylenedioxy group, the heteroaryl moieties specified in the definitions of the above groups refer to a 5-membered heteroaromatic ring, which contains an oxygen, sulphur or nitrogen atom, a nitrogen atom and an oxygen, sulphur or nitrogen atom or two nitrogen atoms and an oxygen, sulphur or nitrogen atom, or a 6-membered heteroaromatic ring, which contains 1, 2 or 3 nitrogen atoms and wherein additionally one or two —CH=N-groups may each be replaced by an —CO—NR$^8$-group, wherein R$^8$ denotes a hydrogen atom or an alkyl group, and additionally the abovementioned heteroaromatic rings may be substituted by one or two alkyl groups or may also be substituted at the carbon skeleton by a fluorine, chlorine, bromine or iodine atom or by a trifluoromethyl, hydroxy or alkyloxy group, and, unless otherwise stated, the abovementioned alkyl, alkylene or alkoxy moieties may each contain 1 to 4 carbon atoms.

However, the preferred compounds of the above general formula I are those wherein X denotes a straight-chained alkylene group having 1 to 3 carbon atoms, which may be substituted by one or two alkyl groups, by an alkenyl group having 2 or 3 carbon atoms, by an alkynyl group having 2 or 3 carbon atoms, by a phenyl, pyridyl, pyridazinyl, pyrimidinyl, pyrazinyl, oxazolyl, thiazolyl, 2-imidazolyl, 4-imidazolyl or 5-imidazolyl group, wherein the abovementioned imidazolyl groups may additionally be substituted by an alkyl group at one of the nitrogen atoms, Z denotes a methylene or ethylene group, each of which may be substituted by one or two alkyl groups, by an alkenyl group having 2 or 3 carbon atoms, by an alkynyl group having 2 or 3 carbon atoms, by a phenyl, pyridyl, pyridazinyl, pyrimidinyl, pyrazinyl, oxazolyl, thiazolyl, 2-imidazolyl, 4-imidazolyl or 5-imidazolyl group, wherein the abovementioned imidazolyl groups may additionally be substituted by an alkyl group at one of the nitrogen atoms, Y denotes a cyclohexylene group optionally substituted by one or two alkyl groups, a piperidinylene group optionally substituted by one or two alkyl groups, wherein one or two methylene groups adjacent to a nitrogen atom may be replaced by a carbonyl group, a piperazinylene group optionally substituted by one or two alkyl groups, wherein one or two methylene groups adjacent to a nitrogen atom may be replaced by a carbonyl group, $R^1$ denotes a hydrogen atom, an alkyl group, an alkyloxycarbonyl group having a total of 2 to 5 carbon atoms or a phenylmethoxycarbonyl group, $R^2$ denotes a hydrogen, fluorine, chlorine, bromine or iodine atom, a trifluoromethyl group, an alkyl or alkoxy group, $R^3$ denotes a hydrogen atom, $R^4$ denotes a hydrogen atom or an alkyl group and $R^5$ denotes a hydrogen atom, an alkyl group having 1 to 8 carbon atoms, a 5- to 7-membered cycloalkyl group or a phenylalkyl group, the tautomers thereof, the stereoisomers including the mixtures thereof and the salts thereof, whilst the phenyl groups mentioned in the definitions of the above groups may each be mono- or disubstituted by a fluorine, chlorine, bromine or iodine atom, by a methyl, trifluoromethyl, hydroxy or methoxy group, and the substituents may be identical or different, and the pyridyl, pyridazinyl, pyrimidinyl, pyrazinyl, oxazolyl or thiazolyl groups mentioned in the definitions of the above groups may each be substituted by a methyl or trifluoromethyl group, and, unless otherwise stated, the abovementioned alkyl and alkoxy moieties may each contain 1 to 4 carbon atoms.

Particularly preferred are the compounds of general formula

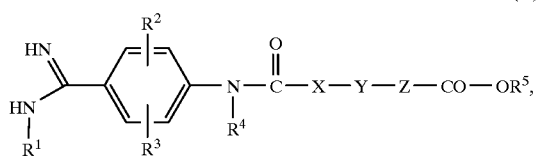

(Ia)

wherein

X denotes a straight-chained alkylene group having 1 to 3 carbon atoms, which may be substituted by one or two alkyl groups each having 1 to 3 carbon atoms, by a vinyl, allyl, ethynyl, propargyl, phenyl, pyridyl, pyrimidinyl, pyridazinyl or pyrazinyl group, wherein the abovementioned phenyl group may additionally be substituted by a fluorine, chlorine, bromine or iodine atom, by a methyl, trifluoromethyl, hydroxy or methoxy group, Z denotes a methylene or ethylene group, each of which may be substituted by one or two alkyl groups each having 1 to 3 carbon atoms, by a vinyl, allyl, ethynyl, propargyl, phenyl, pyridyl, pyrimidinyl, pyridazinyl or pyrazinyl group, wherein the abovementioned phenyl group may additionally be substituted by a fluorine, chlorine, bromine or iodine atom, by a methyl, trifluoromethyl, hydroxy or methoxy group, Y denotes a 1,4-cyclohexylene, 1,4-piperidinylene, 2-oxo-1,4-piperidinylene, 1,4-piperazinylene, 2-oxo-1,4-piperazinylene, 2,3-dioxo-1,4-piperazinylene or 2,5-dioxo-1,4-piperazinylene group, wherein the abovementioned groups may be substituted by one or two alkyl groups each having 1 to 3 carbon atoms, $R^1$ denotes a hydrogen atom, an alkyl group having 1 or 2 carbon atoms, an alkyloxycarbonyl group having a total of 2 or 3 carbon atoms or a benzyloxycarbonyl group, $R^2$ and $R^3$ each denote a hydrogen atom, $R^4$ denotes a hydrogen atom or a methyl group and $R^5$ denotes a hydrogen atom, an alkyl group with 1 to 4 carbon atoms or a cyclohexyl group, particularly those compounds wherein X denotes an ethylene group, which may be substituted by one or two methyl groups, Z denotes a methylene group, which may be substituted by one or two methyl groups, by a pyridyl or phenyl group, wherein the phenyl group may additionally be substituted by a fluorine, chlorine or bromine atom, by a methyl, methoxy or trifluoromethyl group, Y denotes a 1,4-cyclohexylene, 1,4-piperidinylene, 2-oxo-1,4-piperidinylene, 1,4-piperazinylene, 2-oxo-1,4-piperazinylene, 2,3-dioxo-1,4-piperazinylene or 2,5-dioxo-1,4-piperazinylene group, $R^1$ denotes a hydrogen atom, an alkyloxycarbonyl group having a total of 2 or 3 carbon atoms or a benzyloxycarbonyl group, $R^2$, $R^3$ and $R^4$ each denote a hydrogen atom and $R^5$ denotes a hydrogen atom, an alkyl group having 1 to 4 carbon atoms or a cyclohexyl group, the tautomers thereof, the stereoisomers including the mixtures thereof and the salts thereof.

Most particularly preferred compounds of general formula Ia are those wherein

X denotes an ethylene group,

Z denotes a methylene group,

Y denotes a 1,4-piperidinylene group, $R^1$, $R^2$, $R^3$ and $R^4$ each denote a hydrogen atom and $R^5$ denotes a hydrogen atom, an alkyl group having 1 or 2 carbon atoms or a cyclohexyl group, the tautomers thereof, the stereoisomers including the mixtures thereof and the salts thereof.

According to the invention the new compounds of general formula I may be obtained, for example, by the following process:

Reacting a compound of general formula

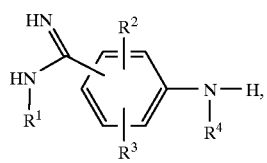

(II)

wherein
R¹ to R⁴ are as hereinbefore defined, with a compound of general formula

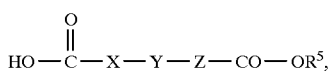

(III)

wherein
R⁵, X, Y and Z are as hereinbefore defined, or the reactive derivatives thereof and
optionally subsequently converting the group R⁵ into a hydrogen atom.

Examples of reactive derivatives of a compound of general formula III include the acid chlorides, acid azides, mixed anhydrides with aliphatic or aromatic carboxylic acids or monocarboxylates, the imidazolides thereof and the esters thereof such as the alkyl, aryl and aralkyl esters thereof, such as the methyl, ethyl, isopropyl, pentyl, phenyl, nitrophenyl or benzyl ester.

The reaction is conveniently carried out in a solvent or mixture of solvents such as methylene chloride, dimethylformamide, dimethylsulphoxide, benzene, toluene, chlorobenzene, tetrahydrofuran, pyridine, pyridine/dimethylformamide, benzene/tetrahydrofuran or dioxane optionally in the presence of a dehydrating agent, e.g. in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, 2-(1H-benzotriazolyl)-1,1,3,3-tetramethyl-uronium salts, N,N'-carbonyldiimidazole, N,N'-thionyldiimidazole or triphenylphosphine/carbon tetrachloride, optionally in the presence of dimethylaminopyridine or 1-hydroxy-benzotriazole and/or a base such as triethylamine, N-ethyl-diisopropylamine, pyridine or N-methyl-morpholine, conveniently at temperatures between −10 and 180° C., preferably at temperatures between 0 and 120° C.

The subsequent conversion of the group R⁵ into a hydrogen atom is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between ambient temperature and the boiling temperature of the reaction mixture.

In the reactions described hereinbefore, any reactive groups present such as carboxy, amino, alkylamino, imino or amidino groups may be protected during the reaction by conventional protective groups which are split off again after the reaction.

For example, the protective group for a carboxyl group may be a trimethylsilyl, methyl, ethyl, tert.butyl, benzyl or tetrahydropyranyl group,
the protective group for an optionally alkyl-substituted amidino group may be a benzyloxycarbonyl group und
the protective group for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group, and for the imino group a methyl group may additionally be considered and for the amino group the phthalyl group is another possibility.

The optional subsequent cleaving of any protective group used may, for example, by carried out hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or by ether splitting, e.g. in the presence of iodotrimethylsilane, at temperatures between 0 and 120° C., preferably at temperatures between 10 and 100° C.

However, a benzyl, methoxybenzyl or benzyloxycarbonyl group is preferably cleaved by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0 and 100° C., but preferably at temperatures between 20 and 60° C., and under a hydrogen pressure of 1 to 7 bar, but preferably 3 to 5 bar. However, a 2,4-dimethoxybenzyl group is preferably cleaved in trifluoroacetic acid in the presence of anisol.

A tert.butyl or tert.butyloxycarbonyl group is, however, preferably cleaved by treatment with an acid such as trifluoroacetic acid or hydrochloric acid or by treatment with iodotrimethylsilane, optionally using a solvent such as methylene chloride, dioxane, methanol or ether.

However, a trifluoroacetyl group is preferably cleaved by treating with an acid such as hydrochloric acid optionally in the presence of a solvent such as acetic acid or methanol at temperatures between 50 and 120° C. or by treating with sodium hydroxide solution optionally in the presence of a solvent such as tetrahydrofuran or methanol at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, as already mentioned hereinbefore, the compounds of general formula I obtained may optionally be resolved into their enantiomers and/or diastereomers. Thus, for example, cis/trans mixtures may be resolved into their cis and trans isomers, and compounds with at least one optically active carbon atom may be resolved into their enantiomers.

Thus, for example, the cis/trans mixtures obtained may be separated into their cis and trans isomers by chromatography, the compounds of general formula I obtained which occur as racemates may be separated into their optical antipodes by methods known per se (cf. Allinger N. L. and Eliel E. L. in "Topics in Stereochemistry", Vol. 6, Wiley Interscience, 1971)) and compounds of general formula I with at least 2 asymmetric carbon atoms may be resolved into their diastereomers on the basis of their physical/chemical differences using methods known per se, e.g. by chromatography and/or fractional crystallisation. If these diastereomers occur in racemic form they may subsequently be resolved into the enantiomers as described above.

The separation of the enantiomers is preferably carried out by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separation of the diastereomeric mixture of salts or derivative thus obtained, e.g. on the basis of differences in solubility, whilst the free antipodes may be released from the pure diastereomeric salts or derivatives by the action of suitable agents. Examples of particularly common optically active acids include the D- and L-forms of tartaric acid or dibenzoyltartaric acid, di-o-tolyltartaric acid, malic acid, mandelic acid, camphorsulphonic acid, glutamic acid, aspartic acid or quinic acid. Examples of optically active alcohols include (+) or (−)-menthol and examples of optically active acyl groups in amides include (+)-or (−)-menthyloxycarbonyl.

Moreover, the compounds of formula I obtained may be converted into the salts thereof, more particularly, for pharmaceutical purposes, the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

Furthermore, the new compounds of formula I obtained, if they contain a carboxyl group, may, if desired, subsequently be converted into the salts thereof with inorganic or organic bases, particularly, for pharmaceutical use, into the physiologically acceptable salts thereof. Examples of bases include sodium hydroxide, potassium hydroxide, arginine, cyclohexylamine, ethanolamine, diethanolamine and triethanolamine.

The compounds used as starting compounds are known from the literature in some cases or may be obtained by methods known from the literature (see Examples).

As already mentioned earlier, the new phenylamidines of general formula I and the salts thereof, particularly the physiologically acceptable salts thereof with inorganic or organic acids or bases, have valuable properties. Thus the new compounds of general formula I have valuable pharmacological properties; in addition to an antiinflammatory effect and the effect of inhibiting bone degradation they also have in particular antithrombotic, antiaggregatory and tumour- and metastasis-inhibiting effects.

For example, the compounds of general formula I were investigated for their biological activities as follows:

1. Inhibiting the Binding of $^3$H-BIBU 52 to Human Thrombocytes:

A suspension of human thrombocytes in plasma is incubated with $^3$H-BIBU 52 [=(3S,5S)-5-[(4'-amidino-4-biphenylyl)oxymethyl]-3-[(carboxy)methyl]-2-pyrrolidinone[3-$^3$H-4-biphenylyl]], replacing the ligand $^{125}$I-fibrinogen known from the literature, (cf. DE-A-4, 214.245) and various concentrations of the substance to be tested. The free and bound ligand is separated off by centrifuging and quantitatively determined by scintillation counting. From the results obtained, the inhibition of $^3$H-BIBU 52 binding by the test substance is determined.

In order to do this, donor blood is taken from an anticubital vein and anticoagulated with trisodium citrate (final concentration 13 mM). The blood is centrifuged for 10 minutes at 170×g and the supernatant platelet-rich plasma (PRP) is removed. The residual blood is sharply centrifuged off once more in order to obtain plasma. The PRP is diluted 1:10 with autologous plasma. 750 μl are incubated with 50 μl of physiological saline, 100 μl of test substance solution, 50 μl of $^{14}$C sucrose (3.700 Bq) and 50 μl of $^3$H-BIBU 52 (final concentration: 5 nM) at ambient temperature for 20 minutes. In order to measure the non-specific binding, 5 μl of BIBU 52 (final concentration: 30 μM) are used instead of the test substance. The samples are centrifuged for 20 seconds at 10,000×g and the supernatant is removed. 100 μl of it are measured in order to determine the free ligand. The pellet is dissolved in 500 μl of 0.2N NaOH, 450 μl are mixed with 2 ml of scintillator and 25 μl of 5N HCl and measured. The residual plasma remaining in the pellet is determined from the $^{14}$C content, and the bound ligand from the measurement of $^3$H. After subtracting the non-specific binding the pellet activity is plotted against the concentration of the test substance and the concentration for a 50% inhibition of binding is determined.

2. Antithrombotic Activity:

Method

The thrombocyte aggregation is measured by the Born and Cross method (J. Physiol. 170, 397 (1964)) in platelet-rich plasma from healthy test subjects. To inhibit clotting, the blood is mixed with 3.14% sodium citrate in a ratio by volume of 1:10.

Collagen-Induced Aggregation

The progress of the decrease in optical density of the platelet suspension is measured photometrically after the addition of the aggregation-triggering substance and recorded. The rate of aggregation is calculated from the angle of inclination of the density curve. The point on the curve at which there is greatest light permeability is used to calculate the optical density.

The quantity of collagen is selected to be as small as possible but still sufficient to produce an irreversible reaction curve. The standard commercial collagen made by Hormonchemie of Munich is used.

Before the collagen is added, the plasma is incubated with the substance at 37° C. for 10 minutes.

From the measurements obtained, an $EC_{50}$ was determined graphically corresponding to a 50% change in the optical density in terms of inhibiting aggregation.

The following Table contains the results found:

| Substance (Example no.) | $^3$H-BIBU-52-binding test $IC_{50}$ [nM] | inhibition of platelet aggregation $EC_{50}$ [nM] |
| --- | --- | --- |
| 1 | 3.7 | 37 |
| 1(1) | 51 | 310 |

In view of their inhibitory effect on cell-to-cell and cell-to-matrix interactions the new cyclic urea derivatives of general formula I and the physiologically acceptable salts thereof are suitable for combating or preventing diseases in which smaller or larger cell aggregations are involved or cell-to-matrix interactions play a part, e.g. in combating or preventing venous and arterial thromboses, cerebrovascular diseases, pulmonary embolisms, cardiac infarct, arteriosclerosis, osteoporosis and tumour metastasis and treating genetically caused or acquired disorders of interactions of cells with one another or with solid structures. They are also suitable for parallel therapy in thrombolysis with fibrinolytics or vascular interventions such as transluminal angioplasty or in the treatment of shock, psoriasis, diabetes and inflammation.

For combating or preventing the above diseases the dosage is between 0.1 μg and 30 mg/kg of body weight, preferably 1 μg to 15 mg/kg of body weight, in up to 4 doses per day. For this purpose the compounds of formula I prepared according to the invention, optionally combined with other active substances such as thromboxane-receptor antagonists and thromboxane synthesis inhibitors or combinations thereof, serotonin antagonists, α-receptor antagonists, alkyl nitrates such as glycerol trinitrate, phosphodiesterase inhibitors, prostacyclin and the analogues thereof, fibrinolytics such as tPA, prourokinase, urokinase, streptokinase, or anticoagulants such as heparin, dermatan sulphate, activated protein C, vitamin K antagonists, hirudine, inhibitors of thrombin or other activated clotting factors, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearyl alcohol, carboxymethylcellulose or fatty substances such as hard fat or suitable mixtures thereof, may be incorporated in conventional galenic preparations such as plain or coated tablets, capsules, powders, suspensions, solutions, sprays or suppositories.

The Examples which follow are intended to illustrate the invention more fully:

EXAMPLE I

4-[2-(chlorocarbonyl)ethyl]-1-[(ethoxycarbonyl)methyl]-piperidine-hydrochloride

To 1.46 g of 4-(2-carboxyethyl)-1-[(ethoxycarbonyl)methyl]-piperidine in 10 ml methylene chloride, is added 1 ml of saturated ethereal hydrochloric acid. 1.2 g of thionyl chloride are added and the mixture is stirred for 3 hours at ambient temperature. The reaction mixture is concentrated by evaporation and the residue is mixed twice with toluene and evaporated down again. The crude product is further reacted in Examples 1 and 2 without being purified.

The following compounds are obtained analogously to Example I:

(1) 1-[2-(chlorocarbonyl)ethyl]-4-[(methoxycarbonyl)methyl]-piperidine-hydrochloride (2) 4-[2-(chlorocarbonyl)ethyl]-1-[(cyclohexyloxycarbonyl)methyl]-piperidine-hydrochloride

EXAMPLE II

4-[2-(carboxy)ethyl]-1-[(ethoxycarbonyl)methyl]-piperidine 10 g of 4-[2-(benzyloxycarbonyl)ethyl]-1-[(ethoxycarbonyl)methyl]-piperidine are hydrogenated in 150 ml of tetrahydrofuran for 4 hours at ambient temperature under a hydrogen pressure of 50 psi in the presence of 1.3 g of palladium on activated charcoal. The reaction mixture is evaporated down and crystallised from diethylether and a little acetone.

yield: 5.8 g of (79% of theory), melting point: 65–67° C.

The following compound is obtained analogously to Example II:

(1) 4-(2-carboxyethyl)-1-[(cyclohexyloxycarbonyl)methyl]-piperidine
melting point: 85–88° C.

EXAMPLE III

4-[2-(benzyloxycarbonyl)ethyl]-1-[(ethoxycarbonyl)methyl]-piperidine

To 9.0 g of 4-[2-(benzyloxycarbonyl)ethyl]-piperidine and 5.2 g of N-ethyl-diisopropylamine in 70 ml of acetonitrile, 6.35 g of ethyl bromoacetate in 20 ml of acetonitrile are added dropwise with stirring in an ice bath and the mixture is stirred for 18 hours at ambient temperature. The reaction mixture is concentrated by evaporation and the residue is quickly divided between tert.butyl-methylether, ice water and 10 ml of 2N sodium hydroxide solution. The organic phase is separated off, washed with ice water and saturated saline solution, dried and concentrated by evaporation.

yield: 10.05 g of (83% of theory), $R_f$ value: 0.84 (silica gel; methylene chloride/methanol/conc. aqueous ammonia=95:5:1).

The following compound is obtained analogously to Example III:

(1) 4-[2-(benzyloxycarbonyl)ethyl]-1-[(cyclohexyloxycarbonyl)methyl]-piperidine
$R_f$ value: 0.47 (silica gel; methylene chloride/methanol/conc. aqueous ammonia=98:2:0,5).

EXAMPLE IV

4-[2-(benzyloxycarbonyl)ethyl]-piperidine 9.7 g of 4-(2-carboxyethyl)piperidine-hydrochloride (melting point: 240–250° C., prepared by hydrogenation of 3-(4-pyridyl)acrylic acid in glacial acetic acid in the presence of platinum oxide and subsequent treatment with hydrochloric acid), 30 ml of benzyl alcohol, 3 g of p-toluenesulphonic acid and 50 ml of toluene are heated for 75 minutes using the water separator. The reaction mixture is concentrated by evaporation in vacuo, the residue is mixed with 50 ml of ice water and extracted three times with tert.butyl-methylether. The aqueous phase is made alkaline and extracted with tert.butyl-methylether. The extract is washed with saline solution, dried and concentrated by evaporation.

yield: 9.0 g (73% of theory), $R_f$ value: 0.18 (silica gel; methylene chloride/methanol/conc. aqueous ammonia=95:5:1).

EXAMPLE V 1-(2-carboxyethyl)-4-[(methoxycarbonyl)methyl]-piperidine-hydrochloride To 2.9 g of 1-[2-(tert.butoxycarbonyl)ethyl]-4-[(methoxycarbonyl)-methyl]-piperidine in 20 ml of methylene chloride are added 10 ml of trifluoroacetic acid and the mixture is stirred overnight at ambient temperature. The reaction mixture is concentrated by evaporation, taken up in acetone, mixed with ethereal hydrochloric acid and again concentrated by evaporation. It is once more taken up in acetone, mixed with ethereal hydrochloric acid and concentrated by evaporation. The residue is stirred with tert.butyl-methylether, to which some acetone has been added, suction filtered and dried.

yield: 2,45 g (92% of theory), $R_f$ value: 0.73 (reversed phase silica gel; methanol/5% aqueous saline solution=6:4).

EXAMPLE VI

1-[2-(tert.butoxycarbonyl)ethyl]-4-[(methoxycarbonyl)methyl]-piperidine

A mixture of 9 ml of tert.butyl acrylate, 10 g of 4-[(methoxycarbonyl)methyl]-piperidine-hydrochloride and 7.2 ml of triethylamine in 150 ml of methanol is refluxed overnight. The reaction mixture is concentrated by evaporation, taken up in methylene chloride and washed twice with saturated sodium hydrogen carbonate solution. The organic phase is separated off, concentrated by evaporation and the residue is purified by chromatography over a silica gel column with methylene chloride/methanol (35:5).

yield: 12.6 g (86% of theory), $R_f$ value: 0.68 (silica gel; methylene chloride/methanol=9:1).

EXAMPLE 1

4-[2-[(4-amidinophenyl)aminocarbonyl]ethyl]-1-carboxymethyl-piperidine×0.2 $H_2O$ To 420 mg of 4-aminobenzamidine-dihydrochloride and 20 mg of 4-dimethylaminopyridine in a mixture of 1.5 ml of dimethylformamide and 1.5 ml of pyridine are added 720 mg of 4-[2-(chlorocarbonyl)ethyl]-1-[(ethoxycarbonyl)methyl]-piperidine-hydrochloride and the mixture is stirred for 1.3 hours at 100° C. The reaction mixture is cooled, mixed with ice water, made alkaline with sodium hydroxide solution and extracted with tert.butyl-methylether and methylene chloride. The aqueous phase is adjusted with hydrochloric acid to a pH value of 3–4 and evaporated to dryness at a bath temperature of 70° C. The residue is heated to boiling with 100 ml of ethanol, after cooling it is filtered and the filtrate is concentrated by evaporation. The evaporation residue is heated with 30 ml of ethanol, it is cooled and the solid is suction filtered. The solid is stirred with 15 ml of tetrahydrofuran and 4.5 ml of 1N sodium hydroxide solution. The mixture is combined with 2.75 ml of 1N hydrochloric acid and stirred over an ice bath. The precipitate is washed with water and tetrahydrofuran and dried in vacuo.

yield: 144 mg (21% of theory), melting point: 283° C. (decomp.). $R_f$ value: 0.76 (reversed phase silica gel; methanol/5% aqueous saline solution=6:4) Calculated: C 60.77, H 7.32, N 16.67 Found: 60.55, 7.26, 16.83 Mass spectrum: $(M+H)^+=333$.

The following compounds are obtained analogously to Example 1:

(1) 1-[2-[(4-amidinophenyl)aminocarbonyl]ethyl]-4-carboxymethyl-piperidine×2 $H_2O$ melting point: 192–200° C. (with sintering and decomposition). $R_f$ value: 0,77 (reversed phase silica gel; methanol/5% aqueous saline solution=6:4) Calculated: C 55.42, H 7.66, N 15.21 Found: 55.02, 7.38, 14.95

(2) 4-[2-[(4-amidinophenyl)aminocarbonyl]ethyl]-1-carboxymethyl-piperazine (3) 4-[2-[(4-amidinophenyl)aminocarbonyl]ethyl]-1-carboxymethyl-2-oxo-piperidine (4) 4-[2-[(4-amidinophenyl)aminocarbonyl]ethyl]-1-carboxymethyl-2-oxo-piperazine (5) 4-[2-[(4-amidinophenyl)aminocarbonyl]ethyl]-1-carboxymethyl-3-methyl-2-oxo-piperazine (6) 4-[2-[(4-amidinophenyl)aminocarbonyl]ethyl]-1-carboxymethyl-2,3-dioxo-piperazine (7) 4-[2-[(4-amidinophenyl)aminocarbonyl]ethyl]-1-carboxymethyl-2,5-dioxo-piperazine (8) 4-[2-[(4-amidinophenyl)aminocarbonyl]ethyl]-1-carboxymethyl-3-oxo-piperazine (9) 4-[2-[(4-amidinophenyl)aminocarbonyl]ethyl]-1-carboxymethyl-cyclohexane

(10) 4-[2-[(4-amidinophenyl)aminocarbonyl]ethyl]-1-(1-carboxyethyl)-piperidine

(11) α-[4-[2-[(4-amidinophenyl)aminocarbonyl]ethyl]-1-piperidinyl]-phenylacetic acid

(12) α-[4-[2-[(4-amidinophenyl)aminocarbonyl]ethyl]-1-piperidinyl]-(3-pyridyl)acetic acid

(13) 4-[2-[(4-amidinophenyl)aminocarbonyl]propyl]-1-carboxymethyl-piperidine

(14) 4-[2-[(4-amidinophenyl)aminocarbonyl]ethyl]-1-carboxymethyl-3,3-dimethyl-2-oxo-piperazine

(15) α-[4-[2-[(4-amidinophenyl)aminocarbonyl]ethyl]-1-piperidinyl]-(4-fluorophenyl)acetic acid

(16) α-[4-[2-[(4-amidinophenyl)aminocarbonyl]ethyl]-1-piperidinyl]-(4-methoxyphenyl)acetic acid

(17) 4-[2-[(4-amidinophenyl)aminocarbonyl]ethyl]-1-(2-carboxyethyl)-piperidine

EXAMPLE 2

4-[2-[(4-amidinophenyl)aminocarbonyl]ethyl]-1-[(ethoxycarbonyl)methyl]-piperidine×2,15 HCl×0.7 $H_2O$ To 625 mg of 4-aminobenzamidine and 30 mg of 4-dimethylaminopyridine in 5 ml of pyridine are added 950 mg of 4-[2-(chlorocarbonyl)ethyl]-1-[(ethoxycarbonyl)methyl]-piperidine-hydrochloride and the mixture is stirred for 1 hour at 100° C. 2 ml of dimethylformamide are added and the mixture is stirred for a further 1.2 hours at 100° C. The reaction mixture is concentrated by evaporation and the residue is stirred twice with tert.butyl-methylether, the solvent being decanted off and discarded each time. The residue is purified by chromatography over aluminium oxide with ethanol. The product is dissolved in ethanol, made slightly acidic with ethereal hydrochloric acid and concentrated by evaporation. The residue is triturated with acetone, the solid is suction filtered and dried.

yield: 335 mg of (25% of theory), $R_f$ value: 0.35 (aluminium oxide; ethanol/conc. aqueous ammonia=99:1) Calculated: C 50.55, H 7.04, N 12.41, Cl 16.88 Found: 50.02, 6.96, 12.51, 17.27 Mass spectrum: $(M+H)^+=361$.

The hydrochlorides of the following compounds are obtained analogously to Example 2:

(1) 1-[2-[(4-amidinophenyl)aminocarbonyl]ethyl]-4-[(ethoxycarbonyl)methyl]-piperidine (2) 4-[2-[(4-amidinophenyl)aminocarbonyl]ethyl]-1-[(ethoxycarbonyl)methyl]-piperazine (3) 4-[2-[(4-amidinophenyl)aminocarbonyl]ethyl]-1-[(ethoxycarbonyl)methyl]-2-oxo-piperidine (4) 4-[2-[(4-amidinophenyl)aminocarbonyl]ethyl]-1-[(ethoxycarbonyl)methyl]-2-oxo-piperazine (5) 4-[2-[(4-amidinophenyl)aminocarbonyl]ethyl]-1-[(ethoxycarbonyl)methyl]-3-methyl-2-oxo-piperazine (6) 4-[2-[(4-amidinophenyl)aminocarbonyl]ethyl]-1-[(ethoxycarbonyl)methyl]-2,3-dioxo-piperazine (7) 4-[2-[(4-amidinophenyl)aminocarbonyl]ethyl]-1-[(ethoxycarbonyl)methyl]-2,5-dioxo-piperazine (8) 4-[2-[(4-amidinophenyl)aminocarbonyl]ethyl]-1-[(ethoxycarbonyl)methyl]-3-oxo-piperazine (9) 4-[2-[(4-amidinophenyl)aminocarbonyl]ethyl]-1-[(ethoxycarbonyl)methyl]-cyclohexane

(10) 4-[2-[(4-amidinophenyl)aminocarbonyl]ethyl]-1-[1-(ethoxycarbonyl)ethyl]-piperidine

(11) ethyl α-[4-[2-[(4-amidinophenyl)aminocarbonyl]ethyl]-1-piperidinyl]-phenylacetate

(12) ethyl α-[4-[2-[(4-amidinophenyl)aminocarbonyl]ethyl]-1-piperidinyl]-(3-pyridyl)acetate

(13) 4-[2-[(4-amidinophenyl)aminocarbonyl]propyl]-1-[(ethoxycarbonyl)methyl]-piperidine

(14) 4-[2-[(4-amidinophenyl)aminocarbonyl]ethyl]-1-[(ethoxycarbonyl)methyl]-3,3-dimethyl-2-oxo-piperazine

(15) ethyl α-[4-[2-[(4-amidinophenyl)aminocarbonyl]ethyl]-1-piperidinyl]-(4-fluorophenyl)acetate

(16) ethyl α-[4-[2-[(4-amidinophenyl)aminocarbonyl]ethyl]-1-piperidinyl]-(4-methoxyphenyl)acetate

(17) 4-[2-[(4-amidinophenyl)aminocarbonyl]ethyl]-1-[2-(ethoxycarbonyl)ethyl]-piperidine

(18) 4-[2-[(4-amidinophenyl)aminocarbonyl]ethyl]-1-[(cyclohexyloxycarbonyl)methyl]-piperidine×2,3 HCl×2 H$_2$O melting point: from 170° C. (decomp.). R$_f$ value: 0.58 (reversed phase silica gel; methanol/5% aqueous saline solution=6:4) Calculated: C 51.69, H 7.60, N 10.48, Cl 15.26 Found: 51.69, 7.46, 10.44, 15.17

EXAMPLE 3

Dry Ampoule Containing 2.5 mg of Active Substance per 1 ml

| Composition: | |
|---|---|
| active substance | 2.5 mg |
| mannitol | 50.0 mg |
| water for injections | ad 1.0 ml |

Method of Preparation:

The active substance and mannitol are dissolved in water. After bottling, the solution is freeze-dried. For use, the solution is made up with water for injections.

EXAMPLE 4

Dry Ampoule Containing 35 mg of Active Substance per 2 ml

| Composition: | |
|---|---|
| active substance | 35.0 mg |
| mannitol | 100.0 mg |
| water for injections | ad 2.0 ml |

Method of Preparation:

The active substance and mannitol are dissolved in water. After packaging, the solution is freeze-dried. For use, the solution is made up with water for injections.

EXAMPLE 5

Tablet Containing 50 mg of Active Substance

| Composition: | |
|---|---|
| (1) active substance | 50.0 mg |
| (2) lactose | 98.0 mg |
| (3) maize starch | 50.0 mg |
| (4) polyvinylpyrrolidone | 15.0 mg |
| (5) magnesium stearate | 2.0 mg |
| | 215.0 mg |

Method of Preparation:

(1), (2) and (3) are mixed together and granulated with an aqueous solution of (4). (5) is added to the dry granulate. From this mixture compressed tablets are produced, which are biplanar, faceted on both sides and provided with a dividing notch on one side.

Diameter of the tablets: 9 mm.

EXAMPLE 6

Tablet Containing 350 mg of Active Substance

| Composition: | |
|---|---|
| (1) active substance | 350.0 mg |
| (2) lactose | 136.0 mg |
| (3) maize starch | 80.0 mg |
| (4) polyvinylpyrrolidone | 30.0 mg |
| (5) magnesium stearate | 4.0 mg |
| | 600.0 mg |

Method of Preparation:

(1), (2) and (3) are mixed together and granulated with an aqueous solution of (4). (5) is added to the dry granulate. From this mixture compressed tablets are produced, which are biplanar, faceted on both sides and provided with a dividing notch on one side.

Diameter of the tablets: 12 mm.

EXAMPLE 7

Capsules Containing 50 mg of Active Substance

| Composition: | |
|---|---|
| (1) active substance | 50.0 mg |
| (2) dried maize starch | 58.0 mg |
| (3) powdered lactose | 50.0 mg |
| (4) magnesium stearate | 2.0 mg |
| | 160.0 mg |

Method of Preparation:

(1) is triturated with (3). This triturated mixture is added to the combination of (2) and (4) with thorough blending.

Using a capsule filling machine this powdered mixture is packed into size 3 hard gelatin capsules.

EXAMPLE 8

Capsules Containing 350 mg of Active Substance

| Composition: | |
|---|---|
| (1) active substance | 350.0 mg |
| (2) dried maize starch | 46.0 mg |
| (3) powdered lactose | 30.0 mg |
| (4) magnesium stearate | 4.0 mg |
| | 430.0 mg |

Method of Preparation:

(1) is triturated with (3). This triturated mixture is added to the combination of (2) and (4) with thorough blending.

Using a capsule filling machine this powdered mixture is packed into size 0 hard gelatin capsules.

We claim:
1. A phenylamidine of formula

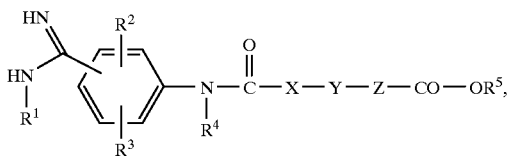

wherein
X and Z, which may be identical or different, each denote a straight-chained alkylene group, which may optionally be substituted by one or two alkyl groups, by an alkenyl group having 2 to 4 carbon atoms, by an alkynyl group having 2 to 4 carbon atoms, by an aryl, arylmethyl, heteroaryl or heteroarylmethyl group, Y denotes an optionally by one or two alkyl groups substituted piperidinylene, 2-oxo-piperidinylene or 2,6-dioxo piperidinylene group, $R^1$ denotes a hydrogen atom, an alkyl, 1,1,1-trifluoroethyl or alkyloxycarbonyl group, an arylalkyloxycarbonyl group having 1 to 3 carbon atoms in the alkyl moiety or a group of formula

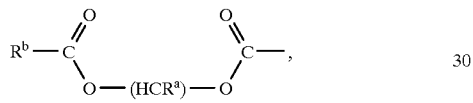

wherein
$R^a$ denotes a hydrogen atom or an alkyl group and
$R^b$ denotes an alkyl group or a 3- to 7-membered cycloalkyl group, $R^2$ and $R^3$, which may be identical or different, each denote a hydrogen, fluorine, chlorine, bromine or iodine atom, an alkyl, trifluoromethyl or alkoxy group, $R^4$ denotes a hydrogen atom, an alkyl, arylalkyl or heteroarylalkyl group and $R^5$ denotes a hydrogen atom, an alkyl group having 1 to 8 carbon atoms, a 4- to 7-membered cycloalkyl group optionally substituted by one or two alkyl groups, an aryl or arylalkyl group or a group of formula

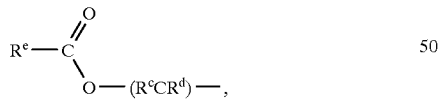

wherein
$R^c$ denotes a hydrogen atom or an alkyl group,
$R^d$ denotes a hydrogen atom or an alkyl group and
$R^e$ denotes an alkyl or alkoxy group, a 3- to 7-membered cycloalkyl gorup or a 5- to 7-membered cycloalkoxy group,
wherein, unless otherwise stated,
the aryl moieties specified in the definitions of the above groups refer to a phenyl group, which may be monosubstituted by $R^6$, mono, di- or trisubstituted by $R^7$ or monosubstituted by $R^6$ and additionally mono- or disubstituted by $R^7$, wherein the substituents may be identical or different and $R^6$ denotes a cyano, carboxy, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoralkyl, trifluoromethoxy, nitro, amino, alkylamino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl- or dialkylaminosulphonyl group and $R^7$ denotes an alkyl, hydroxy or alkoxy group, a fluorine, chlorine, bromine or iodine atom, wherein two groups $R^7$, if they are attached to adjacent carbon atoms, may also denote an alkylene group having 3 to 6 carbon atoms, a 1,3-butadiene-1,4-diylene group or a methylenedioxy group, the heteroaryl moieties specified in the definitions of the above groups refer to a 5-membered heteroaromatic ring, which contains an oxygen, sulphur or imino group, a nitrogen atom and an oxygen, sulphur or imino group or two nitrogen atoms and an oxygen, sulphur or imino group, or a 6-membered heteroaromatic ring, which contains 1, 2 or 3 nitrogen atoms and wherein additionally one or two —CH=N-groups may each be replaced by an —CO—$NR^8$-group, wherein $R^8$ denotes a hydrogen atom or an alkyl group, and additionally the above mentioned heteroaromatic rings may be substituted by one or two alkyl groups or may also be substituted at the carbon skeleton by a fluorine, chlorine, bromine or iodine atom or by a trifluoromethyl, hydroxy or alkyloxy group, and, unless otherwise stated, the above mentioned alkyl, alkylene or alkoxy moieties may each contain 1 to 4 carbon atoms a tautomer thereof, a stereoisomer including a mixture thereof or a salt thereof.

2. The phenylamidine of formula I as recited in claim 1, wherein
X denotes a straight-chained alkylene group having 1 to 3 carbon atoms, which may be substituted by one or two alkyl groups, by an alkenyl group having 2 or 3 carbon atoms, by an alkynyl group having 2 or 3 carbon atoms, by a phenyl, pyridyl, pyridazinyl, pyrimidinyl, pyrazinyl, oxazolyl, thiazolyl, 2-imidazolyl, 4-imidazolyl or 5-imidazolyl group, wherein the above mentioned imidazolyl groups may additionally be substituted by an alkyl group at one of the nitrogen atoms, Z denotes a methylene or ethylene group, each of which may be substituted by one or two alkyl groups, by an alkenyl group having 2 or 3 carbon atoms, by an alkynyl group having 2 or 3 carbon atoms, by a phenyl, pyridyl, pyridazinyl, pyrimidinyl, pyrazinyl, oxazolyl, thiazolyl, 2-imidazolyl, 4-imidazolyl or 5-imidazolyl group, wherein the above mentioned imidazolyl groups may additionally be substituted by an alkyl group at one of the nitrogen atoms, Y denotes an optionally by one or two alkyl groups substituted piperidinylene, 2-oxo-piperidinylene or 2,6-dioxo-piperidinylene group, $R^1$ denotes a hydrogen atom, an alkyl group, an alkyloxycarbonyl groups having a total of 2 to 5 carbon atoms or a phenylmethoxycarbonyl group, R² denotes a hydrogen, fluorine, chlorine, bromine or iodine atom, a trifluoromethyl group, an alkyl or alkoxy group, R³ denotes a hydrogen atom, R⁴ denotes a hydrogen atom or an alkyl group and R⁵ denotes a hydrogen atom, an alkyl group having 1 to 8 carbon atoms, a 5- to 7-membered cycloalkyl group or a phenylalkyl group, whilst the phenyl groups mentioned in the definitions of the above groups may each be mono- or disubstituted by a fluorine, chlorine, bromine or iodine atom, by a methyl, trifluoromethyl, hydroxy or methoxy group, and the substituents may be identical or different, and the pyridyl, pyridazinyl, pyrimidinyl, pyrazinyl, oxazolyl or thiazolyl groups mentioned in the definitions of the above groups may each be substituted by a methyl or trifluoromethyl group, and, unless otherwise stated, the above mentioned alkyl and alkoxy moieties may each contain 1 to 4 carbon atoms, a tautomer thereof, a stereoisomer including a mixture thereof or a salt thereof.

3. The phenylamidine as recited in claim 2, wherein

Y denotes an optionally by one or two $C_{1-4}$-alkyl groups substituted piperidinylene group, a tautomer thereof, a stereoisomer including a mixture thereof or a salt thereof.

4. A phenylamidine of formula

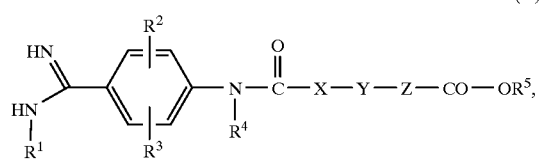

(Ia)

wherein

X denotes a straight-chained alkylene group having 1 to 3 carbon atoms, which may be substituted by one or two alkyl groups each having 1 to 3 carbon atoms, by a vinyl, allyl, ethynyl, propargyl, phenyl, pyridyl, pyrimidinyl, pyridazinyl or pyrazinyl group, wherein the above mentioned phenyl group may additionally be substituted by a fluorine, chlorine, bromine or iodine atom, by a methyl, trifluoromethyl, hydroxy or methoxy groups, Z denotes a methylene or ethylene group, each of which may be substituted by one or two alkyl groups each having 1 to 3 carbon atoms, by a vinyl, allyl, ethynyl, propargyl, phenyl, pyridyl, pyrimidinyl, pyridazinyl or pyrazinyl groups, wherein the above mentioned phenyl group may additionally be substituted by a fluorine, chlorine, bromine or iodine atom, by a methyl, trifluoromethyl, hydroxy or methoxy group, Y denotes an optionally by one or two $C_{1-3}$-alkyl groups substituted piperidinylene group, R¹ denotes a hydrogen atom, an alkyl group having 1 or 2 carbon atoms, an alkyloxycarbonyl group having a total of 2 or 3 carbon atoms or a benzyloxycarbonyl group, R² and R³ each denote a hydrogen atom, R⁴ denotes a hydrogen atom or a methyl group and R⁵ denotes a hydrogen atom, an alkyl group with 1 to 4 carbon atoms or a cyclohexyl group, a tautomer thereof, a stereoisomer including a mixture thereof or a salt thereof.

5. The phenylamidine of formula Ia as recited in claim 4, wherein

X denotes an ethylene group, which may be substituted by one or two methyl groups, Z denotes a methylene group, which may be substituted by one or two methyl groups, by a pyridyl or phenyl group, wherein the phenyl group may additionally be substituted by a fluorine, chlorine or bromine atom, by a methyl, methoxy or trifluoromethyl group, Y denotes a 1,4-piperidinylene group, R¹ denotes a hydrogen atom, an alkyloxycarbonyl group having a total of 2 or 3 carbon atoms or a benzyloxycarbonyl group, R², R³ and R⁴ each denote a hydrogen atom and R⁵ denotes a hydrogen atom, an alkyl group having 1 to 4 carbon atoms or a cyclohexyl group, a tautomer thereof, a stereoisomer including a mixture thereof or a salt thereof.

6. The phenylamidine of formula Ia as recited in claim 4, wherein

X denotes an ethylene group,

Z denotes a methylene group,

Y denotes a 1,4-piperidinylene group,

R¹, R², R³ and R⁴ each denote a hydrogen atom and

R⁵ denotes a hydrogen atom, an alkyl group having 1 or 2 carbon atoms or a cyclohexyl group, a tautomer thereof, a stereoisomer including a mixture thereof or a salt thereof.

7. The phenylamidine of formula I as recited in claim 1, which is

4-[2-[(4-amidinophenyl)aminocarbonyl]ethyl]-1-carboxymethyl-piperidine,

4-[2-[(4-amidinophenyl)aminocarbonyl]ethyl]-1-[(ethoxycarbonyl)-methyl]-piperidine or 4-[2-[(4-amidinophenyl)aminocarbonyl]ethyl]-1-[(cyclohexyl-oxycarbonyl)methyl]-piperidine or a salt thereof.

8. 4-[2-[(4-amidinophenyl)aminocarbonyl]ethyl]-1-carboxymethyl-piperidine or a salt thereof.

9. The physiologically acceptable salt of the phenylamidine as recited in claim 1 with an inorganic or organic acid or base.

10. A pharmaceutical composition of matter comprising a phenylamidine as recited in claim 1 together with one or more inert carriers or diluents.

11. A method for treating or preventing disease in a warm-blooded animal in which smaller or larger cell aggregation occurs or cell-matrix interaction plays a role which comprises administering to the animal a therapeutically effective amount of a phenylamidine as recited in claim 1.

* * * * *